United States Patent [19]

Imamura et al.

[11] Patent Number: 5,026,547
[45] Date of Patent: Jun. 25, 1991

[54] COMPOUND HAVING INSECTICIDAL ACTIVITY AND INSECTICIDE COMPOSITION CONTAINING THE SAME

[75] Inventors: Kei-ichi Imamura; Shuichi Gomi; Michiaki Iwata; Shinji Miyadoh; Masaru Shimura; Takashi Shomura; Masaji Sezaki; Shigeharu Inoye, all of Kanagawa, Japan

[73] Assignee: Meiji Seika Kaisha, Ltd., Tokyo, Japan

[21] Appl. No.: 434,954

[22] Filed: Nov. 9, 1989

[30] Foreign Application Priority Data

Nov. 11, 1988 [JP] Japan ............................... 63-283715

[51] Int. Cl.$^5$ ..................... A61K 35/70; C12P 1/02
[52] U.S. Cl. ..................................... 424/122; 435/171
[58] Field of Search ....................... 424/122; 435/171

Primary Examiner—Jerome D. Goldberg
Attorney, Agent, or Firm—Sughrue, Mion, Zinn, Macpeak & Seas

[57] ABSTRACT

A novel compound having an intense insecticidal activity and a process for producing the same which comprises culturing a strain belonging to the genus Humicola and isolating the compound from the culture.

2 Claims, 4 Drawing Sheets

COMPOUND HAVING INSECTICIDAL ACTIVITY AND INSECTICIDE COMPOSITION CONTAINING THE SAME

FIELD OF THE INVENTION

This invention relates to a novel compound having insecticidal activity and a process for producing the same.

BACKGROUND OF THE INVENTION

Although there are a number of physiologically active substances produced by microorganisms, the number of those showing insecticidal effects is limited. Thus it has been urgently required to develop novel insecticide compounds.

SUMMARY OF THE INVENTION

An object of the present invention to provide a novel compound having insecticidal activity and a process for producing the same.

As a result of intensive investigations, the present inventors found that a novel compound having insecticidal activity can be isolated from the culture of a strain belonging to Denteromycotina.

Thus, the present invention is directed to a novel compound having insecticidal activity (hereinafter referred to as Compound PF1018) and its salts.

The present invention is also directed to a process for producing Compound PF1018 which comprises culturing a Compound PF1018-producing strain belonging to Denteromycotina and isolating Compound PF1018 from the culture.

DETAILED DESCRIPTION OF THE INVENTION

The physicochemical and biological properties of Compound PF1018 according to the present invention are as follows.

Physicochemical properties of Compound PF1018

(1) Appearance: pale yellow grain like crystal.

(2) Elemental analysis as $C_{28}H_{35}NO_3 \cdot H_2O$: calculated: C, 74.47%, H, 8.26%, N, 3.10%. found: C, 75.08%, H, 8.06%, N, 3.38%.

(3) Mass spectrum (FD-MS): m/z 433 (M+).

(4) Melting point: 182°–184 °C.

(5) Specific rotation: $[\alpha]_D^{24} = -185°$ (c 1.0, CHCl$_3$).

Figure 1:
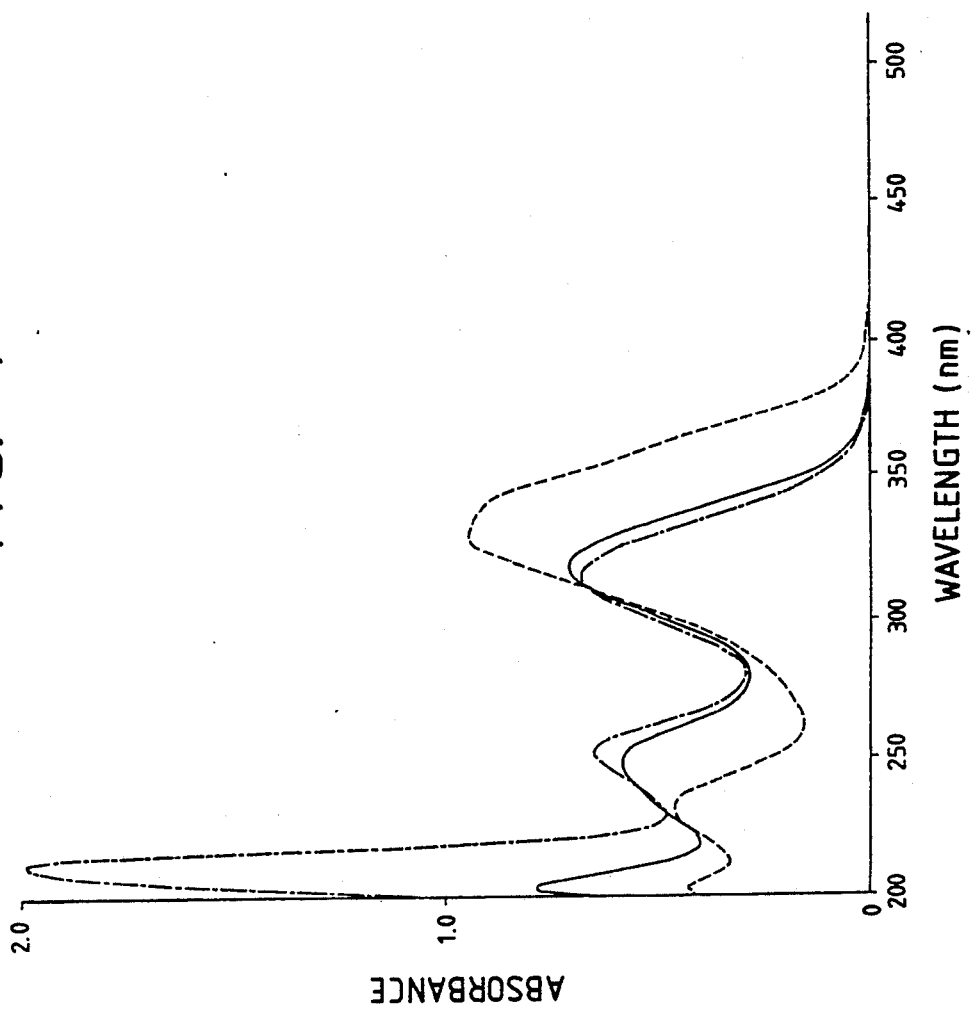
FIG. 1 shows UV and visible spectra of Compound PF1018 in methanol (20 μg/ml, solid line), in acidic methanol (20 μg/ml, broken line) and in basic methanol (20 μg/ml, single-dot chain line).

(6) UV and visible spectra (FIG. 1): $\lambda_{max}$ nm (E$_1$ cm$^{1\%}$).

[MeOH]: 204 (393), 251 (294) and 320 (355). [0.1 N HCl—MeOH]: 204 (215), 235 (229), 332 (471) and 358 (sh 280).

[0.1 N NaOH—MeOH]: 213 (992), 254 (326) and 316 (340).

Figure 2:
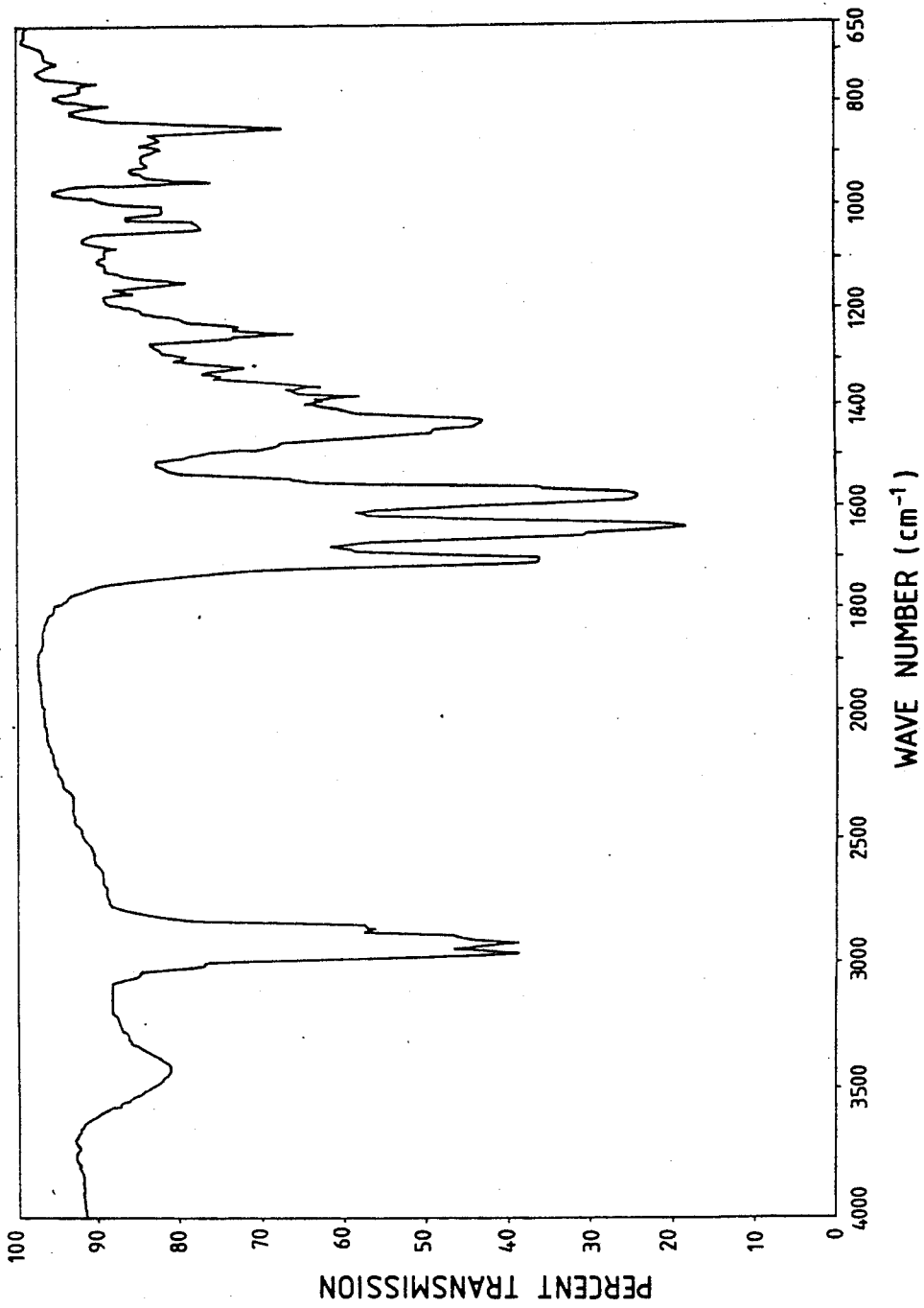
FIG. 2 shows the IR spectrum of Compound PF1018 in a potassium bromide tablet.

(7) IR spectrum (FIG. 2): (KBr cm$^{-1}$): 3410, 2960, 2925, 2870, 1710, 1640, 1580, 1430, 1380, 1360, 1330, 1315, 1290, 1245, 1230, 1165, 1125, 1075, 1040, 1010, 1000, 950, 920, 890, 870, 845, 805, 775, 760 and 720.

Figure 3:
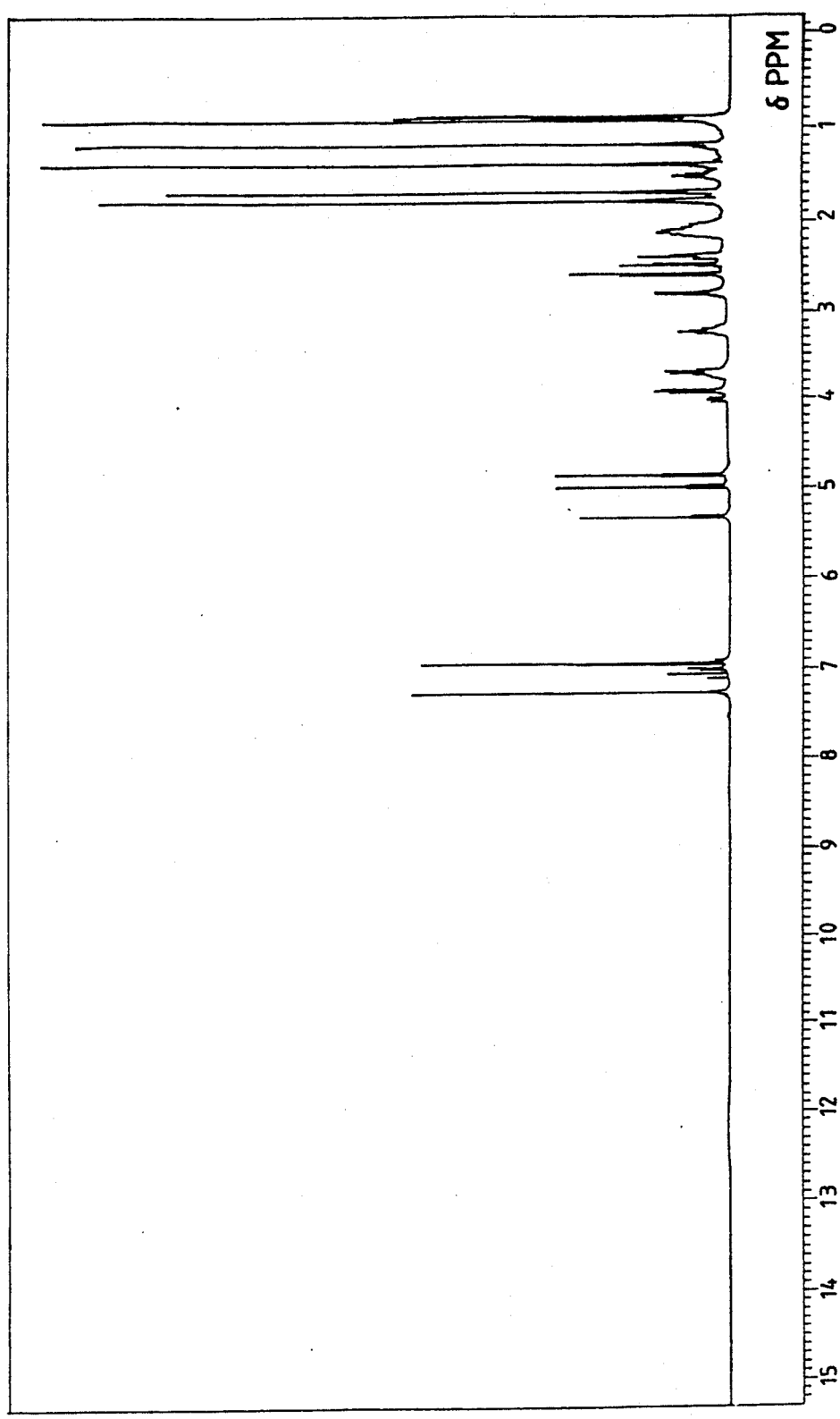
FIG. 3 shows the 400 MHz $^1$H-NMR spectrum of Compound PF1018 in a heavy chloroform solution.

(8) $^1$H NMR spectrum: shown in FIG. 3.

Figure 4:
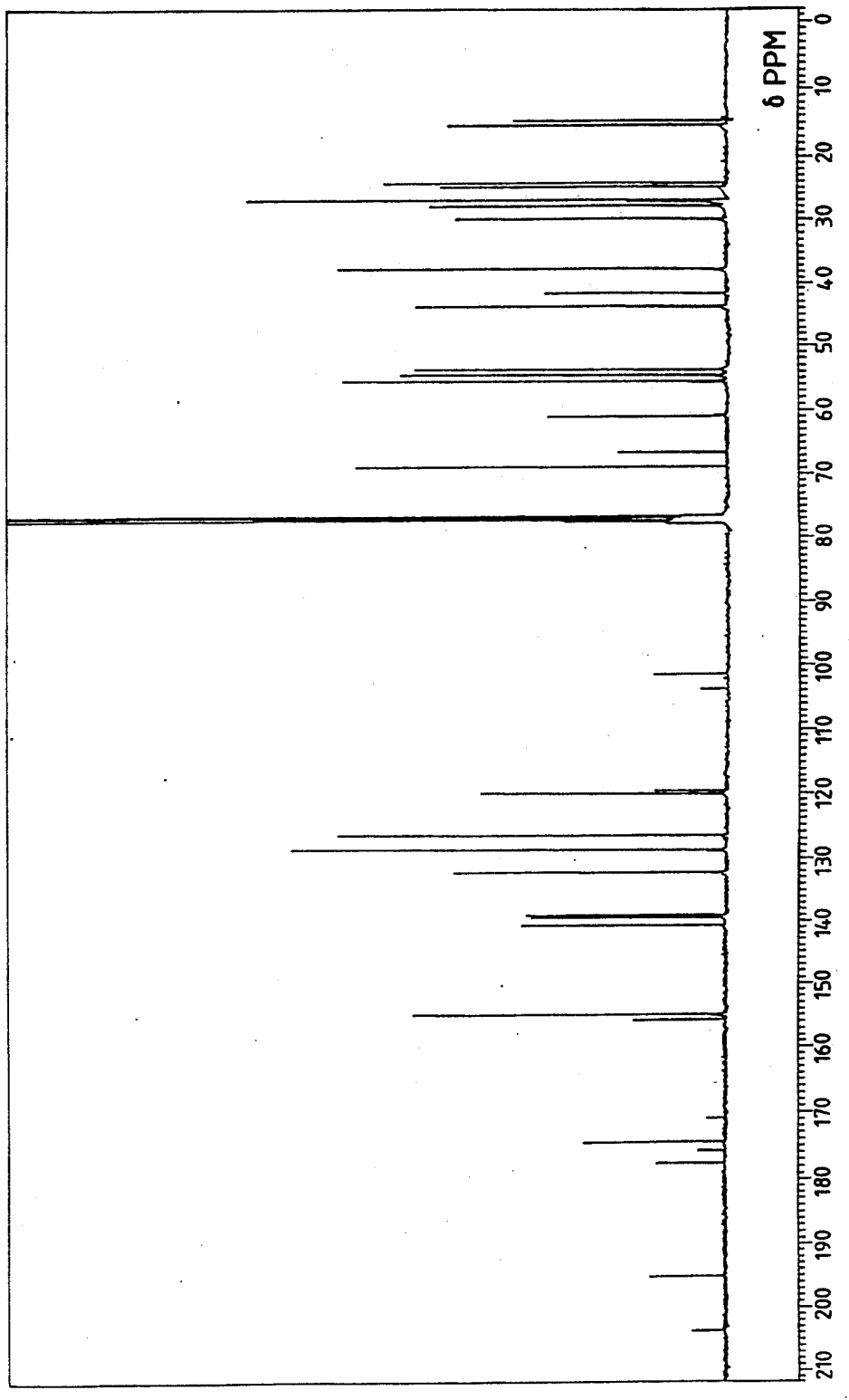
FIG. 4 shows the 100 MHz $^{13}$C NMR spectrum of Compound PF1018 in a heavy chloroform solution.

(9) $^{13}$C NMR spectrum: shown in FIG. 4.

(10) Solubility: soluble in chloroform, ethyl acetate, acetone and methanol but insoluble in water. (11) Basic, acidic or neutral: acidic.

Biological properties of Compound PF1018

Compound PF1018 has an intense insecticidal activity as described in Test Examples below.

Mycological properties of Compound PF1018-producing strain

An example of the Compound PF1018-producing strain to be used in the present invention is strain PF1018 which was isolated from a soil sample collected at Ohmachi-shi, Nagano, Japan for the first time.

Strain PF1018 was cultured on potato-dextrose agar (PDA), potato-carrot agar (PCA) and corn meal agar (CMA) to thereby examine the growth conditions thereof. As a result, it showed almost the same growth on these media. The growth rate at 25° C. for 7 days was 10 mm in a diameter of colony and that for 14 days was 20 to 22 mm, while it showed no growth 37° C. It showed good growth within a pH range of 5 to 7. The colonies had plane surface and were white to gray and cottony. The color of the colony turned to black with the formation of brown to black conidia. The reverse side of the colony changed from orange to black by bearing conidia. No soluble pigment was formed.

The results of microscopic observation are as follows. A conidiophore is colorless and individually extends from aerial hyphae without branching. It is in the form of club or ampul. A conidium is unicellular and has a smooth surface. It is in an ellipsoid form of 6.0–8.4×3.6–4.4 μm. Conidia of this strain are aleurioconidia and are individually formed on the tip and sides of a conidiophore and form no chain. Each conidium has a round top and a cut-end base.

These mycological properties indicate that strain PF1018 is considered to belong to the genus Humicola in accordance with M. B. Ellis [cf. Dematiaceous Hyphomycetes, 59–60, C. M. I., Kew (1971)]. The present inventors named this strain Humicola sp. PF1018. It has been deposited with the Fermentation Research Institute of Agency of Industrial Science and Technology as accession No. FERM BP-2627 under the Budapest treaty.

Similar to other fungi, strain PF1018 has highly changeable properties. Thus, any spontaneous or induced mutant, transductant or genetic recombinant originating from strain PF1018 is available in the present invention so long as it can produce Compound PF1018.

Cultivation of Compound PF1018-producing strain

Compound PF1018-producing microorganism, strain PF1018, may be cultured in a medium containing nutrients commonly utilized by fungi. Conventionally known nutritional sources for culturing fungi may be used therefor. Examples of a carbon source include glucose, starch syrup, dextrin, starch, molasses and animal and vegetable oils. Examples of a nitrogen source include soybean meal, wheat germ, corn steep liquor, cotton seed meal, meat extract, peptone, yeast extract, ammonium sulfate, sodium nitrate and urea. Furthermore, inorganic salts capable of forming ions such as sodium, potassium, calcium, magnesium, cobalt, chlorine, phosphate or sulfate ions may be added, if required. Furthermore, appropriate organic or inorganic materials capable of promoting the growth of the strain and accelerating the production of Compound PF1018 may be added to the medium.

It is preferable to conduct the cultivation under aerobic conditions and submerged culture is the most preferable. The culture may be conducted at 23° to 30° C., suitably around 26° C. The production of Compound PF1018 would show the maximum accumulation within 2 to 7 days either in shaking or tank culture, though it would somewhat vary depending on the medium or culture conditions. When the accumulation of Compound PF1018 in the culture medium reaches the maximum level, the culture is ceased and the desired product is isolated from the medium.

Purification of Compound PF1018

Compound PF1018 obtained by the process of the present invention may be collected from the culture medium by a conventional isolation procedure by taking advantage of its properties, for example, solvent extraction, ion exchange resin method, adsorption or partition column chromatography, gel filtration, dialysis, precipitation or a combination of these procedures. For example, Compound PF1018 may be extracted from the cells with acetone/water, methanol/water or ethyl acetate. On the other hand, Compound PF1018 accumulated in the culture medium may be extracted with an organic solvent immiscible with water such as butanol or ethyl acetate.

Compound PF1018 may be further purified by chromatography with the use of, for example, an adsorbent such as silica gel (Wakogel C-200, mfd. by Wako Pure Chemicals, etc.), alumina, Sephadex ® LH-20 (mfd. by Pharmacia) or Toyopearl ® HW-40 (mfd. by Tosoh).

Suitable developing solvents are chloroform/methanol (100/1 by volume) or hexane/acetone (4/1 by volume) for silica gel (Wakogel C-200) chromatography and methanol for chromatography using Sephadex ® LH-20 or Toyopearl ® HW-40.

The above-described isolation and purification procedures can be performed at room temperature (about 26° C.).

Compound PF1018 thus produced in the culture medium may be isolated in a free-form, namely, Compound PF1018 per se. Alternately, a solution containing Compound PF1018 or a concentrate thereof may be treated with a base, for example, an alkali metal compound such as sodium hydroxide or potassium hydroxide, an alkaline earth metal compound such as calcium hydroxide or magnesium hydroxide, an inorganic base such as an ammonium salt or an organic base such as ethanolamine, triethylamine or dicyclohexylamine during the extraction, isolation or purification step to thereby convert Compound PF1018 into the corresponding salt which is then isolated. The salt of Compound PF1018 thus obtained may be converted into the free form by a conventional method. Furthermore, Compound PF1018 obtained in the free form may be converted into the corresponding salt by a conventional method. Namely, the present invention further involves the above-mentioned salts in addition to Compound PF1018.

The salts of Compound PF1018 according to the present invention are preferably a sodium salt and a calcium salt.

Compound PF1018 shows an insecticidal effect on harmful insects belonging to, for example, Lepidoptera (e.g., *Spodoptera litura, Plutella xylostella, Chilo suppressalis*), Coleptera (e.g., Curculionidae, Chrysomelidae), Diptera (e.g., *Musca domestica, Culex pipiens*), Thysanoptera, Blattaria (e.g., cockroach), Hemiptera (e.g., Aphididae, Delphacidae, Deltocephalidae, Pentatomidae), Orthoptera, Acarina and the like.

Upon using as an insecticide, Compound PF1018 may be used alone or generally formulated with a solid carrier, a liquid carrier, a gaseous carrier, a surfactant, a dispersant, or the other auxiliary or food into an emulsion, a liquid, a wettable powder, a dust, a granule, an oil solution, aerosol, a flowable agent or poisonous food.

Examples of solid carriers include talc, bentonite, clay, kaolin, diatomaceous earch, vermiculite, white carbon and calcium carbonate.

Examples of liquid carriers include alcohols such as methanol, n-hexanol, ethylene glycol and cellosolve, ketones such as acetone, methyl ethyl ketone and cyclohexanon, aliphatic hydrocarbons such as kerosene, aromatic hydrocarbons such as benzene, toluene, xylene and methyl naphthalene, halogenated hydrocarbons such as dichloroethane, trichloroethylene and tetrachlorocarbon, ethers such as diethyl ether, dioxane and tetrahydrofuran, esters such as ethyl acetate, nitriles such as acetonitrile and isobutyronitrile, acid amides such as dimethylformamide and dimethylacetamide, vegetable oil such as soybean oil and cotton seed oil, dimethylsulfoxide or water.

Examples of gaseous carriers include LPG, tetrafluorocarbon, air, nitrogen, carbon dioxide and dimethyl ether.

Examples of surfactants, dispersants used for emulsifying, dispersing or spreading include include alkyl sulfates, alkyl (aryl) sulfonates, polyoxyalkylene alkyl (aryl) ethers, polyvalent alcohol esters or lignin sulfonates.

Examples of auxiliaries for improving the state of the preparation include carboxymethyl cellulose, gum arabic, polyethylene glycol or calcium stearate.

The above-described additives can be used alone or in combination if necessary.

Compound PF1018 is contained in the preparation in an amount of 1 to 50 parts by weight in case of an emulsion, 0.3 to 25 parts by weight in case of dust formulation, 1 to 90 parts by weight in case of a wettable powder and 0.5 to 10 parts by weight in case of granules.

The PF1018 preparation can be used as it is or diluted prior to use. The preparation can be used as a mixture with the other insecticides, miticides, fungicides, bactericides, herbicides, plant growth regulators, fertilizers, soil improving agents or synergists.

The following example further illustrates the present invention. However, it is possible to devise various processes for the production of Compound PF1018 based on the properties thereof which have been disclosed by the present invention. Accordingly, the present invention is not restricted by the following Example but involves not only any modification of said Example but also any process for the production, concentration, extraction and purification of Compound PF1018 comprising known procedures based on the properties of Compound PF1018 which have been disclosed by the present invention.

EXAMPLE

A seed medium comprising 2.0% of starch, 1.0% of glucose, 0.6% of wheat germ, 0.5% of peptone, 0.2% of soybean meal, 0.3% of yeast extract and 0.1% of calcium carbonate was employed. Further, a production medium comprising 2.0% of starch, 2.0% of glucose, 1.0% of soybean meal, 1.0% of wheat germ, 0.5% of meat extract, 0.2% of sodium chloride, 0.3% of calcium carbonate, 0.1% of magnesium sulfate heptahydrate and 0.001% of zinc sulfate heptahydrate was employed. Prior to the sterilization, the pH value of each medium was adjusted to 7.0.

A 100 ml Erlenmeyer flask containing 20 ml of the seed medium was sterilized at 120° C. for 30 minutes and then inoculated with 2 or 3 platinum loopful of Humicola sp. PF1018 (FERM BP-2627) cultured on agar slant. Then, the strain was cultivated under shaking at 26° C. for 5 days to give a first seed culture. Next, a 500 ml Erlenmeyer flask containing 80 ml of the seed medium was sterilized at 120° C. for 30 minutes and then inoculated with 4 ml of the first seed culture. After cultivating under shaking at 26° C. for 3 days, the second seed culture was obtained.

Two 50 l jar fermentors each containing 35 l of the production medium, which had been preliminarily sterilized at 120° C. for 30 minutes, were inoculated with 400 ml portions of the above second seed culture. Then, each culture was cultivated at 26° for 5 days under aeration at 20 l/min. and agitation at 250 rpm in the early stage and at 400 rpm after 41 hours. After the completion of the incubation, diatomaceous earth was added to the culture medium as a filtration aid and the medium was filtrated to give a filtrate and cells.

50 l of a 60% aqueous solution of acetone was added to the cells and the mixture was stirred for 1 hour. After filtering the cells, a cell extract was obtained. The solvent was distilled off from the cell extract under reduced pressure to give 22 l of a concentrate. This concentrate was subjected to extraction with 20 l portions of ethyl acetate twice. After concentrating the ethyl acetate phase, 16 g of an oily substance was obtained. This oily substance was applied a silica gel column (700 g) and chromatographed using a mixture of hexane/acetone (4:1) as a developing solvent. The fraction containing Compound PF1018 which was determined by thin-layer chromatography was collected and concentrated to dryness to give 320 mg of a brown oily substance. This substance was applied on a silica gel column (20 g) and chromatographed using a mixture of chloroform/methanol (100:1) as a development solvent. The crude Compound PF1018-containing fraction thus obtained (232 mg) was further subjected to column chromatography with the use of 600 ml of Sephadex ® LH-20 and methanol as a development solvent. Thus, 216 mg of a pale yellow oily substance was obtained. This pale yellow oily substance was dissolved in 120 ml of chloroform and washed with 120 ml of 0.01 N hydrochloric acid. Then, the chloroform phase was concentrated to dryness and the residue was dissolved in 5 ml of methanol. After concentrating to dryness again, 176 mg of purified Compound PF1018 was obtained as a pale yellow powder. The powder was recrystalized from methanol to give 110 mg of Compound PF1018 as a pale yellow grain like crystal.

In the following Formulation Examples, "part" means "weight by part" unless otherwise specified.

FORMULATION EXAMPLE 1

20 parts of Compound PF1018 was mixed with 20 parts of N,N-dimethylformamide, 30 parts of xylene and 10 parts of polyoxyethylene alkyl aryl ether and the mixture was agitated to obtain an emulsion.

FORMULATION EXAMPLE 2

25 parts of Compound PF1018 was mixed with 30 parts of clay, 35 parts of diatomaceous earch, 3 parts of calcium lignin sulfonate and 7 parts of polyoxyethylene alkyl aryl ether and ground to obtain a wettable powder.

FORMULATION EXAMPLE 3

2 parts of Compound PF1018 was mixed with 60 parts of clay, 37 parts of talc, 1 part of calcium stearate to obtain dust formulation.

FORMULATION EXAMPLE 4

5 parts of Compound PF1018 was mixed with 40 parts of bentonite, 53 parts of talc, 2 parts of calcium lignin sulfonate and ground. After addition of water to the mixture, it was granulated and dried to obtain granules.

TEST EXAMPLE 1

The emulsion obtained in Formulation Example 1 was diluted with water containing 0.05% of Tween-20 ® (ICI) so as to give a concentration of Compound PF1018 of 1,000 ppm. Ten Plutella xylostella of the third instar was immersed in the above suspension for 10 seconds. Then, the insect was fed on a cabbage (5 cm × 5 cm) in a plastic cup (9 cm diameter) at 25° C. After two days of feeding, dead insects were counted and mortality was calculated according to the following equation:

Mortality (%) = (No. of killed insects/No. of tested insects) × 100.

As a result, it was found that the mortality was 100%.

TEST EXAMPLE 2

Ten female Tetranychus cinnbarinus imagos were inoculated on the primary leaf of French bean (*Phasaolus vulgaris*) which had been cultivated in a plastic pot (6 cm diameter). One day after the inoculation of the insects, the wettable powders obtained in Formulation Example 2 were diluted with water containing 0.05% of Tween-20 ® (ICI) so as to give a concentration of Compound PF1018 of 100 ppm and 10 ml of the suspension was scattered into the plastic pot by a sprayer. Then, the insects were fed at 27° C. one more day and the mortality was caluculated in the same manner as in Test Example 1.

As a result, it was found that the mortality was 100%.

TEST EXAMPLE 3

Ten female Musca domestica imagos were anesthetized with ether and an acetone solution containing Compound PF1018 (1.0 μg/μl) was topically applied to the dorsal thorax at a dose of 1 μl by a microsyringe. Then, the insects were fed on absorbent cotton infiltrated with a sucrose solution in a plastic pot (9 cm diameter) at 25° C. After one day of feeding, the mortality was calculated in the same manner as in Test Example 1.

As a result, the mortality was found to be 100%.

As described above, Compound PF1018 of the present invention has an intense insecticidal activity and is expected to be useful as an active ingredient of an insectcide and as a starting material for producing its derivative.

While the invention has been described in detail and with reference to specific embodiments thereof, it will be apparent to one skilled in the art that various changes and modifications can be made therein without departing from the spirit and scope thereof.

What is claimed is:

1. A compound having the following properties:
   (1) Appearance: pale yellow grain like crystal;
   (2) Elemental analysis as $C_{28}H_{35}NO_3 \cdot H_2O$: calculated: C, 74.47%, H, 8.26%, N, 3.10%; found: C, 75.08%, H, 8.06%, N, 3.38%;
   (3) Mass spectrum (FD-MS): m/z 433 (M+);
   (4) Melting point: 182°–184° C.;
   (5) Specific rotation: $[\alpha]_D^{24} = -185°$ (c 1.0, $CHCl_3$);
   (6) UV and visible spectra: shown in FIG. 1;
   (7) IR spectrum: shown in FIG. 2;
   (8) $^1$H NMR spectrum: shown in FIG. 3;
   (9) $^{13}$C NMR spectrum: shown in FIG. 4;
   (10) Solubility: soluble in chloroform, ethyl acetate, acetone and methanol but insoluble in water; and
   (11) Basic, acidic or neutral: acidic or salts thereof.

2. An insecticide composition comprising an insecticidal effective amount of a compound or salts thereof as defined in claim 1 and an acceptable carrier or diluent.

* * * * *